United States Patent [19]

Walder et al.

[11] Patent Number: 5,962,425
[45] Date of Patent: *Oct. 5, 1999

[54] METHODS FOR DECREASING THE EXPRESSION OF SPECIFICALLY TARGETED GENES

[75] Inventors: Joseph A. Walder; Roxanne Y. Walder; Paul S. Eder; John M. Dagle, all of Iowa City, Iowa

[73] Assignee: University of Iowa Research Foundation, Iowa City, Iowa

[*] Notice: This patent is subject to a terminal disclaimer.

[21] Appl. No.: 08/460,704

[22] Filed: Jun. 2, 1995

Related U.S. Application Data

[62] Division of application No. 07/672,088, Mar. 19, 1991, Pat. No. 5,491,133, which is a continuation of application No. 07/126,564, Nov. 30, 1987, abandoned.

[51] Int. Cl.⁶ .................................................. A61K 48/00
[52] U.S. Cl. .......................... 514/44; 536/23.1; 536/23.5; 536/25.1; 536/25.3; 435/6; 435/69.1; 435/320.1; 435/325; 435/91.1; 435/91.2
[58] Field of Search .............................. 514/44; 536/23.1, 536/23.5, 25.1, 25.3; 435/91.1, 91.2, 69.1, 240.2, 320.1, 325, 6

[56] References Cited

U.S. PATENT DOCUMENTS

| | | | |
|---|---|---|---|
| 3,818,109 | 6/1974 | Bechtle | 426/41 |
| 3,968,257 | 7/1976 | Muller | 426/41 |
| 4,511,713 | 4/1985 | Miller et al. | 435/6 |
| 4,521,509 | 6/1985 | Benkovic | 435/6 |
| 4,676,987 | 6/1987 | Ahern et al. | 426/41 |
| 4,698,303 | 10/1987 | Bailey et al. | 435/139 |
| 4,699,793 | 10/1987 | Eguchi et al. | 426/41 |
| 4,800,159 | 1/1989 | Mullis | 435/172.3 |
| 4,806,463 | 2/1989 | Goodchild et al. | 435/5 |
| 5,004,810 | 4/1991 | Draper | 536/24.5 |
| 5,013,830 | 5/1991 | Ohtsuka et al. | 536/25.1 |
| 5,023,243 | 6/1991 | Tullis et al. | 514/44 |
| 5,210,294 | 5/1993 | Mantovani et al. | 562/580 |
| 5,585,479 | 12/1996 | Hoke et al. | 536/24.5 |

FOREIGN PATENT DOCUMENTS

| | | | |
|---|---|---|---|
| 0203870 | 5/1986 | European Pat. Off. | C07H 21/00 |
| 0288163 | 10/1988 | European Pat. Off. | |
| 25555200 | 5/1985 | France | |
| WO 83/01451 | 4/1983 | WIPO | |
| WO 87/07300 | 12/1987 | WIPO | |

OTHER PUBLICATIONS

Dagle et al. (1991) Antisense Research and Development, vol. 1, pp. 11–20.

Minshull et al. (1986) Nucleic Acids Res., vol. 14, No. 16, 6433–6451.

Eckstein (1983) Angewandte Chemie, vol. 22, No. 6, pp. 423–439.

Froehler Tetra Letters 27(46) pp. 5575–5578 (1981).

Minshall et al Nucl Acids Res 14(16) pp. 6433–6451 (1986).
Smith et al Proc Natl Acad Sci 83 pp. 2787–2791 (May 1986).
Eckstein Angewandte Chemie 22(16) pp. 423–439 (1983).
Eckstein et al Biochemistry 16(15) pp. 3429–3432 (1977).
Ross et al J Mol Biol 188 pp. 579–593 (1986).
Putnig et al Proc Natl Acad Sci 78(12) pp. 7350–7354 (1981).
Enzyme Nomenclature, 1979, Academic Press, New York, NY, p. 259.
Miller et al., 1980, "Oligothymidylate Analogues Having Stereoregular, Alternating Methylphosphonate/Phosphodiester Backbones", J. Biol. Chem. 255:9659–9665.
Kunkel et al., 1981, "Deoxynucleoside [1–thio]triphosphates prevent Proofreading During in vitro DNA Synthesis", Proc. Natl. Acad. Sci. USA 78:6734–6738.
Miller et al., 1981, "Biochemical and Biological Effects on Nonionic Nucleic Acid Methylphosphonates", Biochem. 20:1874–1880.
Letsinger et al., 1982, "Use of Trichlorodimethylethyl as a Protecting Group and Tributylphosphine as a Deprotecting Agent in Oligonucleotide Synthesis", J. Am. Chem. Soc. 104:6805–6806.
Gupta et al., 1984, "The Effect of the 3', 5'Thiophosphoryl Linkage on the Exonuclease Activities of T4 Polymerase and the Klenow Fragment", Nucl. Acids Res. 12:5897–5911.
Schreiber et al., 1985, "Selective Protection of in vitro Synthesized cDNA Against Nucleases by Incorporation of Phosphorothiolate–Analogues", Nucl. Acids Res. 13:7663–7673.
Froehler and Matteucci, 1986, "Nucleoside H–Phosphonates: Valuable Intermediates in the Synthesis of Deoxyoligonucleotides", Tett Lett. 27:469–472.
Miller et al., 1986, "Solid–Phase Synthese of Oligodeoxyribonucleoside Methylphosphonates", Biochem. 25:5092–5097.
Toulmé et al., 1986, "Specific Inhibition of mRNA Translation by Complementary Oligonucleotides Covalently Linked to Intercalating Agents", Proc. Natl. Acad. Sci. USA 83:1227–1231.
Matsukura et al., 1987, "Phosphorotiolate Analogs of Oligodeoxynucleotides: Inhibitors of Replication and Cytopathic Effects of Human Immunodeficiency Virus", Proc. Natl. Acad. Sci USA 84:7706–7710.
Morley et al., 1987, "Distribution of Phosphodiesterase I in Normal Human Tissues", J. Histochem. and Cytochem. 35:75–82.

(List continued on next page.)

*Primary Examiner*—Christopher S. F. Low
*Assistant Examiner*—Dave Trong Nguyen
*Attorney, Agent, or Firm*—Pennie & Edmonds, LLP

[57] ABSTRACT

The use of oligodeoxynucleotides modified at the 3'-terminal internucleotide link as therapeutic agents by a method of hybridizing the modified oligonucleotide to a complementary sequence within a targeted mRNA and cleaving the mRNA within the RNA-DNA helix by the enzyme RNaseH to block the expression of the corresponding gene.

25 Claims, 3 Drawing Sheets

OTHER PUBLICATIONS

Ott and Eckstein, 1987, "Protectionof Oligonucleotide Primers Against Degradation by DNA Polymerase I", Biochem. 26:8237–8241.

Petrenko et al., 1988, "Mutagenesis Directed by Phosphotriester Analogues of Oligonucleotides: a Way to Site–Specific Mutagenesis in vivo", FEBS Lett. 238:109–112.

*Oligodeoxynucleotides, Antisense Inhibitors of Gene Expression*, J. Cohen, ed., Macmillan Press, London, England, 1989, pp. 63, 98.

Inoue et al., FEBS Letters, 215(2):327–330 (May 1987).

Stavrianopoulos and Chargaff, 1073, "Purification and Properties of Ribonuclease H of Calf Thymus", Proc. Natl. Acad. Sci. USA 70:1959–1963.

Sheiness et al., 1975, "Possible Relationship of Poly(A) Shortening to mRNA Turnover", Proc. Natl. Acad. Sci. USA 72:1077–1081.

Stryer, 1975, in: *Biochemistry*, W.H. Freeman & Co., San Francisco, CA, p. 558.

Eckstein et al., 1977, "Stereochemistry of Internucleotidic Bond Formation by tRNA Nucleotidyltransferase from Baker's Yeast", Biochemsitry 16:3429–3432.

Stephenson and Zamecnik, 1978, "Inhibition of Rous Sarcoma Viral RNA Translation by a Specific Oligodeoxynucleotide", Proc. Natl. Acad. Sci. USA 75:285–288.

Froehler, 1986, "Deoxynucleoside H–Phosphonate Diester Intermediates in the Synthesis of Internucleotide Phosphate Analogs", Tetrahedron Lett. 27:5575–5578.

Koziokiewicz et al., 1986, "P–Chiral Analogues of Oligodeoxyribonucleotides: Synthesis, Stereochemistry and Enzyme Studies", Chem. Scr. 26:251–260.

Ross and Kobs, 1986, "H4 Histone Messenger RNA Decay in Cell–Free Extracts Initiates at or Near the 3' Terminus and Proceeds 3' to 5'", J. Mol. Biol. 188:579–593.

Walder et al., 1986, "The 35–Nucleotide Spliced Leader Sequence is Common to All Trypanosome Messenger RNA's", Science 233:569–571.

Agrawal and Goodchild, 1987, "Oligodeoxynucleoside Methylphosphonates: Synthesis and Enzymatic Degradation", Tetrahedron Lett. 28:3539–3542.

Brooks, 1987, "Properties and Uses of Restriction Endonucleases", Meth. Enzymol. 152:113–129.

Marcus–Sekura et al., 1987, "Comparative Inhibtion of Chloramphenicol Acetyltranferase Gene Expressiion by Antisense Oligonucleotide Analogues Having Alkyl Phosphotiester, Methylphosphonate and Phosphorothiolate Linkages", Nucl. Acids Res. 15:5749–5763.

Dagle et al., 1990, "Targeted Degradation of mRNA in Xenopus Oocytes and Embryos Directed by Modified Oligonucleotides: Studies of An2 and Cyclin in Embryogenesis", Nucl. Acids Res. 18:4751–4757.

Dagle et al., 1991, "Pathways of Degradation and Mechanism of Action of Antisense Oligonucleotides in *Xenopus laevis* Embryos", Antisense Res. and Devel. 1:11–20.

Potts et al., 1991, "Epithelial–Mesenchymal Transformation of Embryonic Cardiac Endothelial Cells is Inhibited by a Modified Antisense Oligonucleotie to Transforming Growth Factorβ3", Proc. Natl. Acad. Sci. USA 88:1516–1520.

Eckstein, F., 1983, Angewandte Chemie, 22(6), 423–506.

Smith et al., 1986, Proc. Natl. Acad. Sci. USA, 83, 2787–2791.

Minshull et al., 1986, Nucleic Acids Research, 14(16), 6433–6451.

Ross et al., 1986, Molec. Cell. Biol., 6(12), 4362–4371.

Putney et al., 1981, Proc. Natl. Acad. Sci. USA, 78(12), 7350–7354.

*Webster's II NewRiverside University Dictionary*, 1984, Houghton Mifflin Company, Boston, MA, p. 67.

Porteous et al., 1993, TIBTECH, 11, 173–181.

Wagner, R. W., 1994, Nature, 372, 333–335.

Webb, 1984, *Enzyme Nomenclature*, Academic Press, Orlando, FL, pp. 302–303.

Promega Catalog, 1991–1992, Promega Corp., Madison, WI, p. 243.

Henderson, 1995, Infectious Disease Weekly, (Oct. 23, 1995).

Gura et al. (1995) Science 270: 575–577.

Genesis Report–Rx (Jun. 1993) vol. 4, No. 2.

Disease Weekly (Oct. 23, 1995) Chas. W. Henderson, Publ.

Wu–Pong (Oct. 1994) Pharmaceutical Technol (pp. 102–114).

Stein et al. (1994) Antisense Res. and Develop. 4:67–69.

Edelman (Meeting–Future Needs and Developments in Antisense Technology, Sep. 25–26, 1997, National Institutes of Health (National Heart, Lung & Blood Institute), Bethesda, MD), abstract, p. 14.

Branch (Feb. 1998) TIBS 23 45–50.

Stull et al. (1995) Pharm. Res. 12(4): 465–483.

FIG_4

FIG_5

METHODS FOR DECREASING THE EXPRESSION OF SPECIFICALLY TARGETED GENES

This is a division of application Ser. No. 07/672,088, filed Mar. 19, 1991, now U.S. Pat. No. 5,491,133, which is a continuation of Ser.No. 07/126,564, filed on Nov. 30, 1987, now abandoned.

GRANT REFERENCE

The invention described herein was made in part in the course of work under grants from the National Institutes of Health, Grant Nos. HL-33555 and AM-25295.

BACKGROUND OF THE INVENTION

It is well known that nucleic acids, i.e., deoxyribonucleic acids (DNA) and ribonucleic acids (RNA) are essential building blocks in living cells. These compounds are high molecular weight polymers which are made up of many "nucleotide" units, each such nucleotide unit being composed of a base (a purine or a pyrimidine), a sugar (which is either ribose or deoxyribose) and a molecule of phosphoric acid. DNA contains deoxyribose as the sugar moiety and the bases adenine, guanine, cytosine, and thymine (which may be represented as A, G, C and T, respectively). RNA contains ribose instead of deoxyribose and uracil (U) in place of thymine.

The nucleotide units in DNA and RNA are assembled in definite linear sequences which determine specific biological functions. In the normal mammalian cell, DNA replicates itself, and also serves as the template for the synthesis of RNA molecules whose nucleotide sequences carry the information encoded by the DNA. RNA molecules serve several different functions within the cell. Messenger RNA (mRNA) directs protein synthesis.

According to the well known Watson-Crick model, DNA molecules consist of two polynucleotide strands coiled about a common axis. The resulting double helix is held together by hydrogen bonds between complementary base pairs in each strand. Hydrogen bonds are formed only between adenine (A) and thymine (T) and between guanine (G) and cytosine (C). Hence within the double helix, adenine (A) and thymine (T) are viewed as complementary bases which bind to each other as A-T. The same is true for guanine (G) and cytosine (C), as G-C.

In a single polynucleotide strand, any sequence of nucleotides is possible. However, once the order of bases within one strand of a DNA molecule is specified, the exact sequence of the other strand is simultaneously determined due to the indicated base pairing. Accordingly, each strand of a DNA molecule is the complement of the other. In the process of DNA replication, the two strands act as templates for the synthesis of two new chains with complementary nucleotide sequences. The net result is the production of two new DNA molecules each containing one of the original strands plus a newly synthesized strand that is complementary to it. This process is referred to as semiconservative replication and allows the genetic information encoded within the DNA, specified by the nucleotide sequence, to be transmitted from one generation to the next.

Collectively, the genetic information of an organism is termed the genome. The genome of bacteria and of all higher species is composed of DNA. The genome of viruses may be either DNA or RNA. In any case, the genome of any particular species, whether a virus, bacteria, or higher organism has a characteristic nucleotide sequence which, stated simply, can be viewed as the "fingerprint" of that species.

In the process of transcription, DNA is copied, or transcribed, into RNA. The RNA molecule that is synthesized is single stranded. Its nucleotide sequence is complementary to a segment of one of the two strands of the DNA molecule, and hence it is an exact copy of the opposite strand except that thymine is replaced with uracil. The length of DNA that is copied to form a single RNA molecule represents one gene. The human genome contains approximately 50,000 genes.

Messenger RNAs (mRNAs) carry the coding information necessary for protein synthesis. The sequence of nucleotides in the mRNA molecule specifies the arrangement of amino acids in the protein whose synthesis will be directed by that mRNA. Each set of three nucleotides, a unit called a codon, specifies a particular amino acid. The process by which mRNAs direct protein synthesis is termed translation. Translation of mRNAs occurs on ribosomes within the cytoplasm of the cell.

The flow of information from gene to protein can thus be represented by the following scheme:

$$\text{Gene} \xrightarrow{\text{Transcription}} \text{mRNA} \xrightarrow{\text{Translation}} \text{Protein}$$

For each protein made by an organism there exists a corresponding gene.

It is generally known in the field of molecular biology that oligodeoxyribonucleotides, short single-stranded DNA fragments, having a nucleotide sequence complementary to a portion of a specified mRNA may be used to block the expression of the corresponding gene. This occurs by hybridization (binding) of the oligonucleotide to the mRNA, according to the rules of base pairing described above, which then prevents translation of the mRNA. It has now been discovered that the inhibition of translation observed is due to cleavage of the mRNA by the enzyme RNaseH at the site of the RNA-DNA double helix formed with the oligonucleotide (see FIG. 1). Hybridization of the oligonucleotide to the mRNA is generally not sufficient in itself to significantly inhibit translation. Evidently an oligonucleotide bound to mRNA can be stripped off in the process of translation. An important corollary of this result is that for any modified oligonucleotide to efficiently block expression of a gene, the hybrid formed with the selected mRNA must be recognized by RNaseH and the mRNA cleaved by the enzyme.

Figure 1:
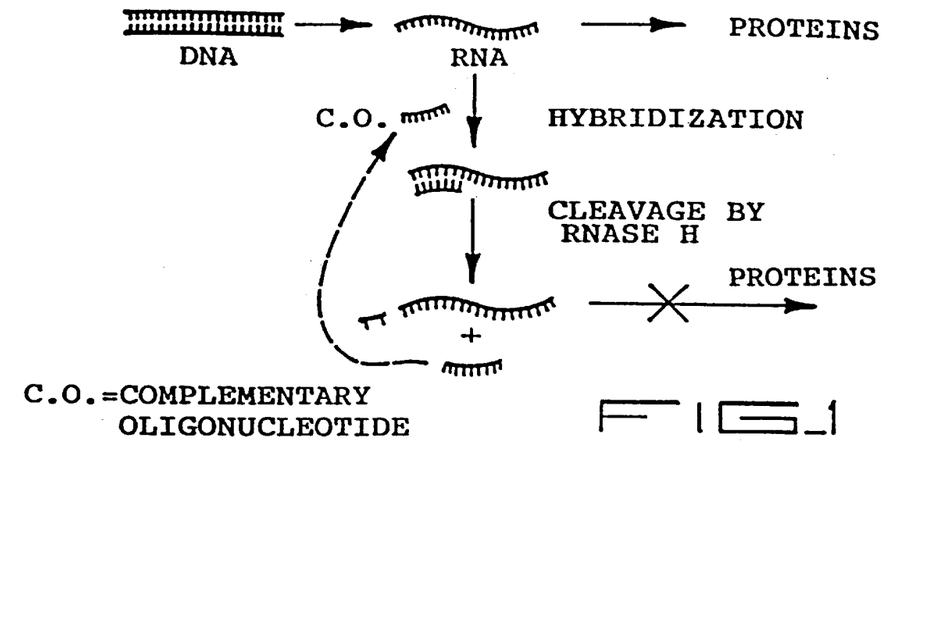
FIG. 1 is a schematic illustration to show how the expression of a selected gene is blocked in accordance with the process of this invention by hybridization of an oligonucleotide to its complementary sequence within the mRNA and cleavage of the mRNA by the enzyme RNaseH at the site of the RNA-DNA double helix.

The process of hybrid-arrested translation outlined in FIG. 1 has obvious implications for the use of oligonucleotides as therapeutic agents. By selectively blocking the expression of a particular gene essential for the replication of a certain virus or bacteria an oligonucleotide could serve as an antimicrobial agent. Similarly, an oligonucleotide targeted against a gene responsible or required for the uncontrolled proliferation of a cancer cell would be useful as an anticancer agent. There are also applications in the treatment of genetic diseases such as sickle cell disease and thalassemia for which no adequate treatment currently exists. Any gene can be targeted by this approach. The problem of drug specificity, a major hurdle in the development of conventional chemotherapeutic agents, is immediately solved by choosing the appropriate oligonucleotide sequence complementary to the selected mRNA. This circumvents toxicity resulting from a lack of selectivity of the drug, a serious limitation of all existing antiviral and anticancer agents.

In addition to the use of oligonucleotides to block the expression of selected genes for the treatment of diseases in man, other applications are also recognized. Additional applications include but are not limited to the use of such oligonucleotides in veterinary medicine, as pesticides or fungicides, and in industrial or agricultural processes in which it is desirable to inhibit the expression of a particular gene by an organism utilized in that process.

A major problem limiting the utility of oligonucleotides as therapeutic agents is the rapid degradation of the oligonucleotide in blood and within cells. Enzymes which degrade DNA or RNA are termed nucleases. Such enzymes hydrolyze the phosphodiester bonds joining the nucleotides within a DNA or RNA chain, thereby cleaving the molecule into smaller fragments.

In the past there has been some progress made in the development of oligonucleotide analogs that are resistant to nuclease degradation, but the use of such derivatives to block the expression of specifically targeted genes has met with limited success. See, for example, Ts'o et al. U.S. Pat. No. 4,469,863 issued Sep. 4, 1984; Miller et al. U.S. Pat. No. 4,507,433 issued Mar. 26, 1985; and Miller et al. U.S. Pat. No. 4,511,713 issued Apr. 16, 1985. Each of the above patents have in common the objective of blocking the expression of selected genes, but the approach taken has been less than successful judging from the high concentrations of oligonucleotide required and a corresponding lack of selectivity. The work described in each of the three prior patents mentioned involves the use of oligonucleotides in which all of the phosphate groups have been modified in the form of methylphosphonates:

Normal Nucleotide Phosphodiester    Methylphosphonate Diester

B, and B$_2$ are nucleic acid bases (either A, G, C or T).

In particular, U.S. Pat. No. 4,469,863 involves inter alia, methylphosphonate modification of oligonucleotides. U.S. Pat. No. 4,507,433 involves a process for synthesizing deoxyribonucleotide methylphosphonates on polystyrene supports; and U.S. Pat. No. 4,511,713 involves determining the base sequence of a nucleic acid and hybridizing to it an appropriately synthesized oligonucleotide methylphosphonate to interfere with its function.

The low level of activity observed using these fully modified methylphosphonate analogs led us to suspect that they would not form effective substrates for RNaseH when hybridized with mRNAs. Results presented in Example 2 show this to be the case.

Figure 2:
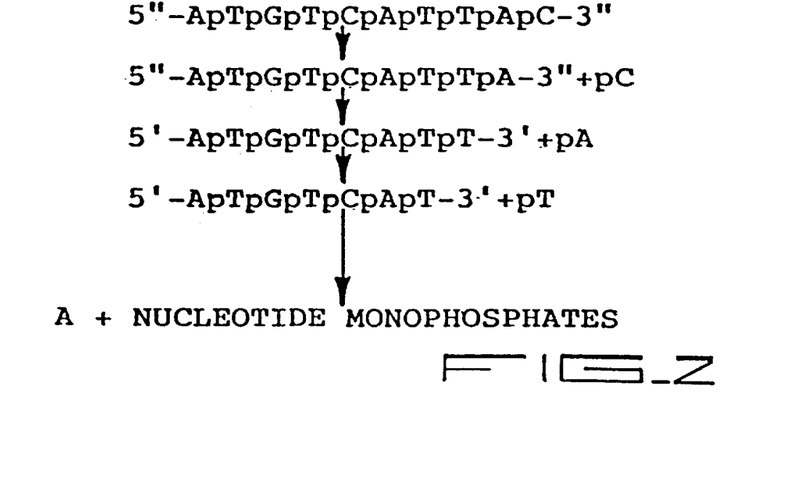
FIG. 2 illustrates the degradation of a single stranded DNA molecule by the action of a nuclease that removes sequentially one nucleotide at a time from the 3'- to the 5'-end of the chain.

In an effort to design new oligonucleotide analogs of greater use as therapeutic agents, we undertook a study of the pathways by which oligonucleotides are degraded within blood and within cells. We have discovered that the sole pathway of degradation in blood (Example 3) and the predominant pathway in cells (Example 4) is via sequential degradation from the 3'-end to the 5'-end of the DNA chain in which one nucleotide is removed at a time. This pathway of degradation is illustrated in FIG. 2. These results provided for the first time a rational basis for the design of oligonucleotide analogs modified so as to inhibit their degradation without interfering with their ability to form substrates for RNaseH.

It has now been discovered that oligonucleotides modified at only the 3'-most internucleotide link are markedly protected from degradation within blood and within cells (Examples 5 and 6). Moreover, we have found that such derivatives have normal hybridization properties and do form substrates with mRNAs that are recognized and cleaved by RNaseH, thereby preventing expression of the targeted gene (Example 7).

The accomplishment of the inhibition of expression of selected genes by oligonucleotides that are resistant to degradation, and that are, therefore, more effective when used therapeutically, is the primary objective of this invention.

Other objectives of the present invention include the preparation of oligonucleotides modified at the 3'-phosphodiester linkage and the formulation of the modified oligonucleotide in a manner suitable for therapeutic use. It is also apparent that DNA or RNA molecules so modified would be useful as hybridization probes for diagnostic applications, in which case, the modification of the 3'-internucleotide link would inhibit degradation of the probe by nucleases which may be present within the test sample.

SUMMARY OF THE INVENTION

The invention comprises the method, means and composition which together enable the use of oligonucleotides that are modified at the 3'-terminal phosphodiester linkage, and are thereby rendered resistant to degradation within cells and body fluids, to selectively block the expression of a particular gene. The method involves the hybridization of the modified oligonucleotide to the corresponding mRNA to form a substrate fully capable of being recognized by the enzyme RNaseH, followed by the cleavage of the mRNA at the site of the RNA-DNA double helix such that the expression of the targeted gene is blocked. The invention further details the use of DNA and RNA molecules modified at the 3'-terminal phosphodiester linkage as nucleic acid probes for diagnostic applications.

DETAILED DESCRIPTION OF THE INVENTION

In the broadest terms, the objectives of the present invention are accomplished by modifying oligonucleotides at just the 3'-terminal phosphodiester linkage. When this is accomplished it has been found that the oligonucleotide is markedly resistant to degradation by nucleases within cells and within blood. Equally important, such modified oligonucleotides hybridize normally with complementary nucleic acid sequences and do form substrates with mRNAs that are recognized and cleaved by RNaseH. As a result of the cleave of the mRNA, expression of the corresponding gene is selectively blocked as is desired in various therapeutic applications.

Recent advances in molecular biology employing recombinant DNA techniques have led to new diagnostic and therapeutic strategies. In DNA diagnostics, a DNA or RNA probe is used to detect the presence of a complementary nucleic acid (DNA or RNA) sequence. In this process the probe hybridizes to its complementary sequence if it is present within the sample. The target sequence may be a DNA or RNA molecule of a bacteria or virus, or an altered gene leading to a genetic abnormality such as sickle cell disease. Frequently, the sample to be analyzed is immobilized on a solid support such as nitrocellulose or a nylon membrane. The probe carries a label, e.g., a radioactive, fluorescent, or enzyme marker to permit its detection. The field of DNA diagnostics is currently under very active investigation, having applications in the diagnosis of infectious diseases, cancer, and genetic disorders. However, there are as yet no products in widespread clinical use. Existing methods, although extremely useful as research tools, lack adequate sensitivity for many practical applications, and are often too complicated to be carried out routinely and reliably in a clinical laboratory.

In DNA therapeutics, an oligonucleotide is used to block the expression of a specifically targeted gene by hybridizing to a complementary sequence within the corresponding mRNA and preventing the mRNA from being translated. In this manner, synthesis of the protein encoded by the gene is blocked. Such is the basic concept employed in each of the above three mentioned prior patents.

However, recent studies which formed the essence of the present invention have shown that blocking of the expression of the targeted gene occurs not simply by the hybridization of the oligonucleotide to the mRNA, but requires that the RNA-DNA double helix so formed serve as a substrate for the enzyme RNaseH. RNaseH, a ubiquitous enzyme required for DNA replication, then digests the mRNA at the RNA-DNA duplex. Only the mRNA is cleaved. The oligonucleotide is released intact and can react repeatedly with other mRNA molecules as indicated by the dashed line in FIG. 1. The effect of each molecule of the oligonucleotide is thereby amplified, increasing the efficiency by which the expression of the targeted gene is blocked.

RNaseH acts only on RNA-DNA double helices. RNA-RNA duplexes do not serve as substrates for the enzyme. Therefore, oligodeoxyribonucleotides (short single-stranded DNA fragments) are preferred as therapeutic agents, rather than RNA molecules. Either RNA or DNA molecules can be used as probes for diagnostic purposes.

One problem faced in both DNA diagnostics and DNA therapeutics is the degradation of the DNA or RNA molecule used either as a probe or therapeutic agent by hydrolytic enzymes, termed nucleases, present in body fluids and tissues. This problem is of far greater concern in the case of DNA therapeutics. Oligonucleotides are degraded in blood, and even more rapidly within cells, the rate of degradation being sufficiently fast to completely abrogate the effect of the drug. In preparing clinical samples for DNA diagnostic tests, efforts are made to remove contaminating nucleases. However, low levels of activity may remain. In certain instances, particularly when applied to genetic tests, the detection method is based on specific cleavage of the probe when it is hybridized to the target sequence. Non-specific degradation of the probe can give rise to an increased level of background signal, obscuring detection of the target-dependent cleavage of the probe.

Nucleases catalyze the degradation of DNA or RNA strands by hydrolysis of the phosphodiester bonds which join the nucleotide units within the chain, thereby cleaving the molecule into smaller fragments. DNA or RNA molecules useful as hybridization probes range from approximately 15 nucleotides in length to over several thousand nucleotides. DNA fragments useful as therapeutic agents range from about 10 to about 75 nucleotides in length, preferably from 15 to 35 nucleotides. Thus, any DNA or RNA molecule used as a probe or therapeutic agent would have many potential sites at which cleavage by nucleases may occur.

It is generally known in the field of molecular biology that phosphodiester linkages normally subject to enzymatic cleavage by nucleases can be protected by modifying the phosphate group. Earlier efforts, such as the three mentioned patents, have focused on derivatives in which all of the phosphate groups within the strand are modified, or on derivatives in which the phosphate groups are extensively modified in a random fashion following the synthesis of the oligonucleotide (Tullis, R. H., P.C.T. WO83/01451, 1983). Such modifications, however, often interfere with hybridization of the DNA to its target sequence, and consequently limits its utility for both diagnostic and therapeutic applications. Moreover, it has been found that DNA fragments in which the phosphate groups are extensively modified do not form substrates for RNaseH (Example 2). This abrogates their use as therapeutic agents.

While not wishing to be bound by any theory, the important discoveries underlying the present invention are: (1) that the mechanism by which oligonucleotides used as therapeutic agents block the expression of specifically targeted genes is to hybridize to the corresponding mRNA, forming a substrate for RNaseH which then cleaves the mRNA; and (2) that the exclusive pathway of degradation of oligonucleotides in blood, and the predominant pathway within cells, is via sequential degradation from the 3'- to the 5'- end of the chain as outlined in FIG. 2. It has thus proven possible to greatly increase the stability of DNA fragments by modification of only the first internucleotide link from the 3'- end of the DNA molecule. When this is done, cleavage of the first nucleotide unit is blocked, and no further degradation can proceed. A variety of substitutions at the 3'- terminal internucleotide link, as explained below, will serve this purpose, the position of the modification being the important factor. As demonstrated in Example 7, such modified derivatives have normal hybridization properties and do form substrates with mRNAs that are recognized and cleaved by RNaseH. Such modified oligonucleotides, thus, are useful for both diagnostic and therapeutic applications.

Oligonucleotides, although highly negatively charged molecules, do enter cells at a finite rate. This was first suggested by a study carried out by Zamecnik and Stephenson (Proceedings of the National Academy of Sciences USA (1978) 75, 280–284 and 285–288), in which an oligonucleotide complementary to the 5'- and 3'-repeat sequences of Rous sarcoma virus were found to inhibit viral replication and the synthesis of viral proteins in chick embryo fibroblasts. In these studies, the mechanism of action of the oligonucleotide was not established, nor was the possiblity that the effects observed were due to degradation products of the oligonucleotide ruled out. Nonetheless, this study, with more recent work, Heikkila et al., Nature (1987) 328, 445–449, indicates that oligonucleotides do enter cells. Zamecnik and Stephenson also showed that the activity of the oligonucleotide could be substantially increased by modifying the 3'-OH and 5'-OH groups with large apolar substituents, i.e., phenyl and naphthyl groups. These large apolar groups enhance the binding of the oligonucleotide to the cell membrane and transport into the cell. The introduction of these groups may also have inhibited the degradation of the oligonucleotide by exonucleases. However, only by directly modifying the phosphodiester group is it possible to preclude cleavage of the internucleotide link within a DNA or RNA strand. Neither the degradation of the native oligonucleotide nor the modified derivatives were studied in this work. Even the most recent study of the degradation of oligonucleotides is completely silent as to the pathway by which degradation occurs (Wickstrom, E. (1986) Journal of Biochemical and Biophysical Methods 13, 97–102).

Thus, while there has been some study of the degradation of DNA and RNA by endogenous nucleases within human and other mammalian tissues previously, it has not hitherto-fore been appreciated that degradation of single-stranded DNA molecules occurs predominantly by a 3'- to 5'-exonucleolytic mechanism. Hence the unique value of the modified derivatives claimed herein could not have been predicted. Put another way, because the pathway of degradation had not been established, no basis existed for the design of DNA molecules in which only selected phosphate groups within the chain were modified to effect an increase in stability, such that the resulting oligonucleotide still hybridized to mRNAs to form substrates that are recognized and cleaved by RNaseH, as is required for use of the oligonucleotide in therapeutic applications.

As heretofore mentioned, the exact chemical modification at the 3'-phosphodiester linkage is not as important as that the modification be at this precise location. A limited number of other positions on the molecule may also be modified without departing from the scope of this invention. In the case of DNA diagnostics, it is necessary to attach a label onto the nucleic acid probe to enable its detection. A radioactive, fluorescent, electrochemical, chemilumenescent or enzyme marker may serve this purpose. For oligonucleotide probes ranging in length from 15 to about 35 nucleotides in length generally only one label is appended to the molecule. Longer DNA or RNA molecules used as probes may be up to several thousand nucleotides in length. In this case the label may be introduced at a density of up to 1 for every 15 nucleotide units in the chain.

For applications in DNA therapeutics, the oligonucleotide may be modified at positions in addition to the 3'-phosphodiester linkage to increase its stability further or to facilitate its transport into cells. Transport of the oligonucleotide into the target cell may be enhanced by attachment to a carrier molecule normally taken up by the cell such as transferrin the plasma iron binding protein, or epidermal growth factor, or the oligonucleotide may be attached to an antibody against a surface protein of the target cell as in the case of the so-called immunotoxins. Alternatively, additional phosphate groups of the oligonucleotide may be modified to reduce the negative charge on the molecule and thereby facilitate its transport across the lipid bilayer of the cell membrane. With such modifications, apolar substituents such as hydrocarbon chains or aromatic groups may also be incorporated into the molecule to further enhance intracellular uptake. Modification of additional phosphate groups within the chain may also increase the stability of the oligonucleotide further by blocking the activity of 5'- to 3'-exonucleases and endonucleases that are present in certain cells (see Example 4). Although degradation by these pathways is much less rapid than degradation from the 3'-end of the chain, the added effect of blocking these activities as well, particularly 5'- to 3'-exonucleolytic cleavage, may be beneficial in many cases. In these various applications, however, it is important that the modifications be restricted to a limited number of the phosphodiester groups. If most or all of the phosphodiester linkages within the chain are modified this will frequently interfere with the hybridization properties of the oligonucleotide, and more importantly, it will preclude the use of such derivatives as therapeutic agents because they will no longer form substrates with targeted mRNAs that are acted upon by RNaseH. It is essential that there be one or more continuous stretches of the oligonucleotide chain in which the phosphodiester linkages are unmodified. The length of this unmodified portion of the chain must be at least 4 nucleotides, and preferably greater than 7 nucleotides in length. When this is accomplished, the oligonucleotide will be protected from degradation due to the modification of the 3'-terminal phosphodiester linkage, and will also hybridize with mRNAs to form substrates for RNaseH, which will cleave the mRNA across from the unmodified portion of the oligonucleotide, enabling the use of such derivatives as therapeutic agents to block the expression of selected genes. The method of modifying the 3'-phosphodiester linkage will now be described.

The modifying moiety is not critical. It can be selected from any of the following functionalities:

alkyl or aryl phosphotriesters alkyl or aryl phosphonates hydrogen phosphonates alkyl or aryl phosphoramidates phosphorothioates phosphoroselenates

In these structures, R may vary in length from 1 to about 20 carbon atoms, and may contain halogen substituents (as in Examples 5 and 6) or other heteroatoms, e.g., N, O, or S, attached to the chain. The methods required to prepare these derivatives are simple, straight-forward reactions well known to those skilled in the art. See for example, the following literature references, each of which discloses modifications of the type expressed herein: Letsinger, et al., Journal of the American Chemical Society, (1982), 104, 6805–6806; Stec et al., Journal of the American Chemical Society (1984), 106, 6077–6079; Miller et al., Biochemistry (1986), 25, 5092–5097; and Froehler, et al., Tetrahedron Letters, (1986), 27, 469–472.

The preferred modification is a phosphotriester, for simplicity of synthesis and the diversity of functional groups which may be attached to the phosphorus atom. Incorporation of a large hydrophobic substituent at this position, for example, may be utilized to facilitate intracellular uptake. As demonstrated in the present work, phosphotriesters are also resistant to hydrolysis by nucleases, and when incorporated at only a limited number of positions within an oligonucleotide chain, the molecule remains able to hybridize normally with mRNAs to form substrates which are cleaved by RNaseH.

In all methods now commonly used, oligonucleotides are synthesized from the 3'- to the 5'-end of the chain. The first residue is coupled to a solid support, such as controlled pore glass, through the 3'-OH group. If the synthesis is carried out in solution, rather than on a solid support, the 3'-OH of the first residue is blocked by a protecting group which is removed at the culmination of the synthesis. Usually, one nucleotide unit is added at a time to the 5'-OH group of the growing chain. Alternatively, a block of several residues may be added in a single reaction. There are several methods by which the internucleotide link to the 5'-OH group may be formed. These procedures are reviewed in the following monograph, "Oligonucleotide Synthesis: A Practical Approach" (Gait, M. J., ed) IRL Press, Oxford (1984), which is incorporated herein by reference. The following reaction scheme illustrates the phosphoramidite method, the preferred chemistry at present.

-continued

DMT is the dimethoxytrityl protecting group; S.S. is the solid support on which the synthesis is carried out. B$_1$ and B$_2$ are nucleic acid bases (either A, G, C or T).

The immediate product of this reaction is a phosphotriester. At the end of the synthesis, the protecting group R is removed to yield a phosphodiester linkage. Typically, the β-cyanoethyl group is used for this purpose. Alternatively, R may be a group which is not removed, in which case the final product is a phosphotriester, the group R remaining permanently attached to the phosphorus atom. It is in this manner that a modified phosphotriester may be incorporated at the first internucleotide linkage from the 3'-end of the chain. By essentially the same chemistry an alkyl or aryl phosphonate may be introduced specifically at this position, in which instance the group R is attached directly to the phosphorous atom rather than through oxygen. Similarly, a hydrogen phosphonate may be introduced at this position. Such derivatives may be used directly, or oxidized to give phosphotriesters or phosphoramidates incorporated at the 3'-terminal internucleotide linkage. The following reference discloses modifications of the hydrogen phosphonate group, Froehler, B. C., Tetrahedron Letters, (1986), 27, 5575–5578. A phosphorothioate or phosphoroselenate group may be incorporated at the 3'-terminal internucleotide link by carrying out the oxidation step in the phosphoramidite method with sulfur, or KSeCN, respectively, Stec. et al., Journal of the American Chemical Society, (1984), 106, 6077–6079. At the completion of the synthesis, following the removal of all protecting groups, the final product may be used directly or further purified by chromatographic methods well known to those skilled in the art, see for example "Oligonucleotide Synthesis: A Practical Approach" (Gait, M. J., ed.) IRL Press, Oxford (1984).

The procedures just described are generally applicable for the synthesis of oligonucleotides up to approximately 100 residues in length. In order to synthesize a longer DNA or RNA molecule in which the 3'-terminal phosphodiester group is modified, as may be required for use as a hybridization probe in diagnostic tests, a combination of both chemical and enzymatic methods is used. To accomplish the synthesis of such a sequence, a short oligonucleotide in which the 3'-terminal phosphodiester linkage was modified, prepared by chemical methods, is enzymatically ligated onto the 3'-OH group of a longer DNA or RNA chain.

Methods of formulation and administration of the modified oligonucleotides described herein are obvious to those of ordinary skill in the medical arts, see for example, Avis, K. (1985) in Remington's Pharmaceutical Sciences, (Gennaro, A. R., ed) pp. 1518–1541, Mack Publishing Company, Easton, Pa., which is incorporated herein by reference. Such methods of administration may include but are not limited to topical, oral, or parenteral routes depending on the disease state. Appropriate vehicles for parenteral administration include 5% dextrose, normal saline, Ringer's solution and Ringer's lactate. The material, of course, must be sterile and substantially endotoxin free. It may be possible in certain cases to store the product as a lyophilized powder which would then be reconstituted when needed by addition of an appropriate salt solution.

The following examples are offered to further illustrate, but not limit, the process, product and medical techniques of the invention, and serve to point out the unique features of the invention which enable it to overcome limitations of earlier contributions to the field.

EXAMPLE 1

Demonstration that the Inhibition of Translation of a Targeted mRNA by a Complementary Oligonucleotide is Dependent on the Cleavage of the mRNA by RNaseH For the purpose of these experiments two oligonucleotides were synthesized: 5'-GAGCACCATGGTTTC, MA-15; ands 5'-TGTCCAAGTGATTCAGGCCATCGTT, CODMB-25. Both were prepared on a Beckman automated DNA synthesizer using the phophoramidite method. MA-15 is complementary to a sequence within mouse α-globin mRNA spanning the initiation codon. CODMB-25 hybridizes to a sequence within the coding region of mouse β-globin mRNA. Mouse globin mRNA was isolated from reticulocytes obtained from mice rendered anemic by treatment with phenylhydrazine as described by Goosens and Kan (Methods in Enzymology (Antonini, E., Rossi-Bernadi, L., and Chiancone, E., eds.) 76, 805–817, 1981). In vitro translation reactions were carried out in the rabbit reticulocyte lysate system. The reticylocyte lysates used were purchased from ProMega Biotec, and contain RNaseH. Translation reactions were programmed with 1 ug of total mouse reticulocyte RNA. The reactions were allowed to proceed for 1 hour at 30° C. Each sample contained 45 uCi of [$^{35}$S]methionine (Amersham) in a total volume of 25 ul. Protein synthesis was measured by incorporation of [$^{35}$S] methionine into material precipitatable in 10% trichloracetic acid. In control reactions in the absence of oligonucleotide, synthesis of β globin accounts for 60% of the incorporated counts; α globin synthesis accounts for 40% of the radioactivity incorporated into protein. Reactions were carried out in both the presence and absence of poly rA/oligo dT (500 ug/ml). Poly rA/oligo dT is a competitive inhibitor of RNaseH, and at the concentration used almost completely blocks the activity of the enzyme. Both MA-15 and CODMB-25 very effectively inhibited translation of the targeted mRNA (see Table 1). MA-15 is complementary to 12 of 15 residues in the corresponding sequence of β-globin mRNA, and, therefore, also inhibits β-globin synthesis to some extent. Poly rA/oligo dT completely blocked the inhibitory effect of the oligonucleotides, indicating that the arrest of translation is mediated entirely by the cleavage of the mRNA by RNaseH.

TABLE 1

Role of RNaseH in Hybrid-Arrested Translation

| Oligonucleotide | % Inhibition of Globin Synthesis | |
|---|---|---|
| | − poly rA/oligo dT | + poly rA/oligo dT |
| MA-15 (8 M) | 51 | 3 |
| CODMB-25 (4 um) | 61 | 5 |

EXAMPLE 2

Oligodeoxynucleotide Methylphosphonates Do Not Form Substrates for RNaseH

Two related substrates for RNaseH were compared: poly rA/oligo dT$_{12-18}$ and poly rA/oligo dT$_{18}$ methylphosphonate (MP). Oligo dT $_{12-18}$ was purchased from Pharmacia PL Biochemicals; the chain length varies from 12 to 18 residues. Oligo dT $_{18}$MP was synthesized on a Beckman automated DNA synthesizer using the phosphonamidite method. The 5'-terminal internucleotide link is a normal phosphodiester; the remaining 16 phosphate groups in the chain are methylphosphonates. Poly rA labeled with tritium was purchased from Amersham.

Each reaction was conducted in a final volume of 100 ul containing 44 picomoles of the substrate, either $^3$H-poly rA/oligo dT$_{12-18}$ or $^3$H-poly rA/oligo dT$_{18}$MP, in 50 mM Tris-HCl buffer pH 8.0, 20 mM KCl, 9 mM MgCl$_2$, 1 mM 2-mercaptoethanol and 25 ug of bovine serum albumin. The reaction was initiated by the addition of 2.3 units of E. coli RNaseH (Bethesda Research Laboratories) and allowed to proceeed for 30 minutes at 37° C. After the reaction, 0.2 ml of carrier DNA solution (0.5 mg/ml of salmon sperm DNA, 0.1 M sodium pyrophosphate, and 1 mM ethylenediamine tetraacetic acid) plus 0.3 ml of 10% trichloracetic acid was added to each sample. The tubes were then incubated on ice for 20 minutes, and afterwards centrifuged at 16,000×g for 15 minutes. Cleavage of the poly rA strand by RNaseH releases smaller fragments that are not precipitated by trichloroacetic acid, and hence remain in the supernatant. The supernatant was carefully removed, mixed with liquid scintillation cocktail, and counted for radioactivity. The reaction with poly rA/oligo dT proceeded nearly to completion—85% of the radioactive counts were solubilized. In contrast, less than 1% of poly rA/oligo dT$_{18}$MP was digested by the enzyme. Thus, when much or all of the phosphate backbone of an oligodeoxynucleotide analogue is modified, it does not form a substrate with the complementary RNA sequence that is recognized and cleaved by RNaseH.

EXAMPLE 3

Oligonucleotides are Degraded in Blood Exclusively by a 3'- to 5'-Exonucleolytic Activity The purpose of this study was to establish the pathways by which oligonucleotides are degraded in blood. Surprisingly, a single pathway was observed: sequential degradation from the 3'- to the 5'-end of the DNA molecule.

The oligonucleotide MA-15 described in Example 1 was radioactively labeled with $^{32}$P at the 5'- end of the molecule using γ$^{32}$P-adenosine triphosphate (γ$^{32}$P-ATP, Amersham) and T4 polynucleotide kinase (Bethesda Research Laboratories):

5-*GAGCACCATGGTTTC where the asterisk represents the radiolabel. Separately, a radiolabeled derivative was prepared in which $^{32}$P was introduced at the 3'most internucleotide link using α$^{32}$P-deoxycytidine triphosphate (dCTP) and DNA polymerase I (Bethesda Research Laboratories):

5'-GAGCACCATGGTTT*C

The reaction catalyzed by DNA polymerase I is between 5'-GAGCACCATGGTTT and dCTP and requires the complementary DNA strand as a template. A 50 fold excess of unlabeled MA-15 was added after the reaction to insure that the labeled derivative is single stranded. These procedures are standard methods for radiolabeling DNA fragments, see for example, Maniatis, T., Fritsch, E. F., and Sambrook, J., *Molecular Cloning: A Laboratory Manual*, Cold Spring Harbor Laboratory, New York, pp. 114–115 and 122–126, 1982, which is incorporated herein by reference.

Figure 3:
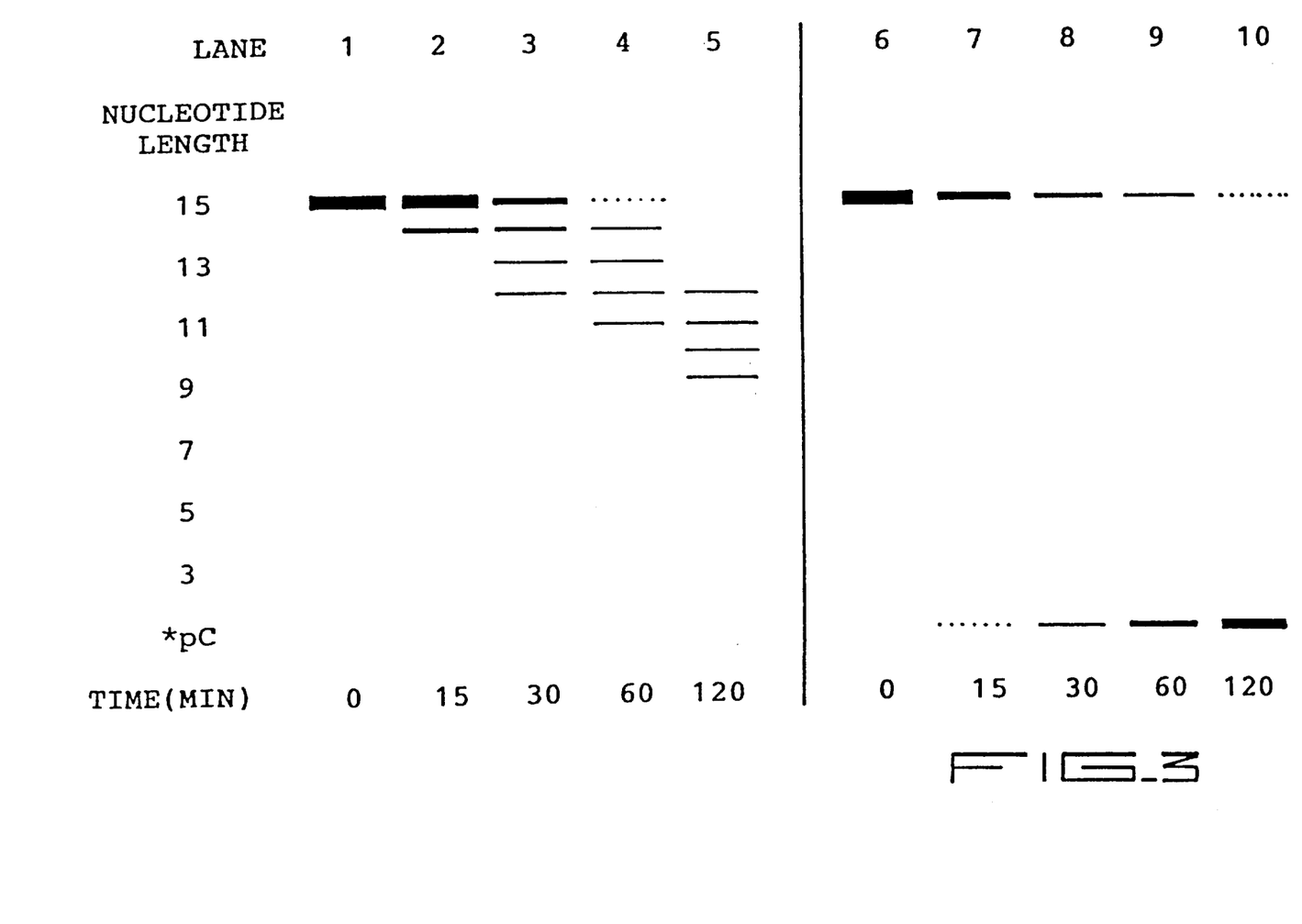
FIG. 3 is a drawing of an autoradiogram demonstrating that the exclusive pathway of degradation of DNA fragments in human blood is by exonucleolytic cleavage from the 3'- to the 5'-end of the DNA chain. The oligonucleotide utilized in this experiment, MA-15, has the sequence: 5'-GAGCACCATGGTTTC. In lanes 1–5, the oligonucleotide was radiolabeled at the 5'-end of the molecule with $^{32}$P. In lanes 6–10, the $^{32}$P-label is at the 3'-terminal internucleotide link. The labeled oligonucleotide was incubated in human blood at 37° C. Aliquots were removed at the times shown and analyzed by polyacrylamide gel electrophoresis. The labeled bands within the gel were visualized by autoradiography.

The radiolabeled oligonucleotide (5×10$^5$ counts/min) plus 2.5 nanomoles of unlabeled MA-15 were added to 48 ul of freshly drawn human blood anticoagulated with heparin. Samples were incubated at 37° C., body temperature. Aliquots of 6 ul were removed at 15 minutes, 30 minutes, 1 hour, and 2 hours. A fraction of each aliquot was loaded onto a polyacrylamide gel and electrophoresed to separate the products on the basis of size. To visualize the radiolabeled products, the gel was exposed to x-ray film overnight. A drawing of the autoradiogram is shown in FIG. 3.

Degradation of the oligonucleotide labeled at the 5'-end of the molecule (lanes 1–5) gave rise to a ladder of discrete products of decreasing size indicative of sequential exonucleolytic cleavage of the strand from the 3'- toward the 5'-end of the chain. Had cleavage occurred within the middle of the strand, products of intermediate length would have appeared throughout the time course. When MA-15 was labeled at the 3'-end of the molecule, the resulting autoradiogram, lanes 6–10, showed, over time, disappearance of the full-length 15-mer, and a corresponding increase in the mononucleotide pC. This result likewise demonstrates a 3'- to 5'-exonucleolytic activity. The lack of products of intermediate size rules out the presence of a 5'- to 3'-exonucleolytic activity, or an endonucleolytic (internal) cleavage activity.

By the same methods as just described, we showed that in blood from other mammalian species, specifically mouse, rabbit, and rat, oligonucleotides are also degraded solely by sequential cleavage of mononucleotides from the 3'-end of the chain.

EXAMPLE 4

The Principal Pathway of Degradation of Oligonucleotides in Human Cells is by Sequential Exonucleolytic Cleavage of the Strand From the 3'- to the 5'- End of the Chain The purpose of these studies was to determine the pathways by which oligonucleotides are degraded by nucleases present within human cells. Radiolabeled derivatives of MA-15 were prepared as in Example 3. Degradation of the oligonucleotide was studied in extracts prepared from the human erythroleukemia cell line K562. The K562 cell line was first isolated by Lozzio, C. B., and Lozzio, B. B., Blood (1975) 45, 321–334, and has been studied extensively as a model for red cell differentiation. The cells were suspended in 10 mM tris buffer pH 7.4 with 5 mM MgCl$_2$, 1 mM CaCl$_2$, 100 mM NaCl, and 0.1% TRITON® X-100 (polyethylene glycol 4-isooctylphenyl ether) and homogenized with a motor-driven cold TEFLON™ (poly-tetrafluoroethylene) pestle homogenizer for 30 seconds. Cell membranes and organelles were further disrupted by sonication by five 15 second bursts using a Biosonic sonifier set on full power. Remaining cell debris was removed from the extracts by centrifugation for 5 minutes at 12,000×g.

The radiolabeled oligonucleotide was incubated in K562 cell extracts under the same conditions as decribed in Example 3 and the degradation products analyzed by polyacrylamide gel electrophoresis. Degradation of the oligonucleotide was much faster than that in blood. The primary pathway of degradation was again a 3' to 5' exonucleolytic activity. The half-life for cleavage of the 3'-terminal internucleotide link was 2 minutes. A slower 5'- to 3'-exonucleolytic activity was also observed. The half-life for cleavage of the 5'-terminal nucleotide unit from the chain by this mechanism was 20 minutes.

Using the same methods as above, the pathways of degradation of oligonucleotides in extracts prepared from other mammalian cells have also been studied. These systems include African green monkey kidney cells (COS cells) and mouse liver cells. The results suggested a low level of endonucleolytic activity (cleavage in the middle of the strand), as well as a 5'- to 3'-exonuclease, but again the major pathway of degradation of the oligonucleotide in each of these systems was by a 3'- to 5'-exonuclease.

EXAMPLE 5

Modification of Oligonucleotides at the 3'-Terminal Internucleotide Link Completely Blocks Their Degradation in Human Blood A derivative of the oligonucleotide MA-15 was prepared in which the first internucleotide link from the 3'-end of the molecule was modified as a 2,2,2-trichloro-1,1- dimethylethyl phosphotriester. The phosphotriester was introduced into the chain using the corresponding phosphorodichloridite:

To 20 micromoles of 5'-deoxythymidine dissolved in 1 cc of 10% pyridine in acetonitrile was added 19 micromoles of the phosphorodichlorodite. The reaction was allowed to proceed for 5 minutes at room temperature. The resulting monochlorodite was added to 1 micromole of deoxycytidine attached to controlled pore glass beads (American Bionetics). The coupling reaction to produce the dinucleotide phosphotriester was allowed to proceed for 15 minutes at room temperature. Excess reagents and by-products of the reaction were washed away with anhydrous acetonitrile. The remaining portion of the DNA strand was synthesized by the β-cyanoethyl phosphoramidite method on a Beckman automated DNA synthesizer. Only the 3'-terminal internucleotide link is modified. The remaining 13 phosphate groups in the chain are normal phosphodiesters.

Figure 4:
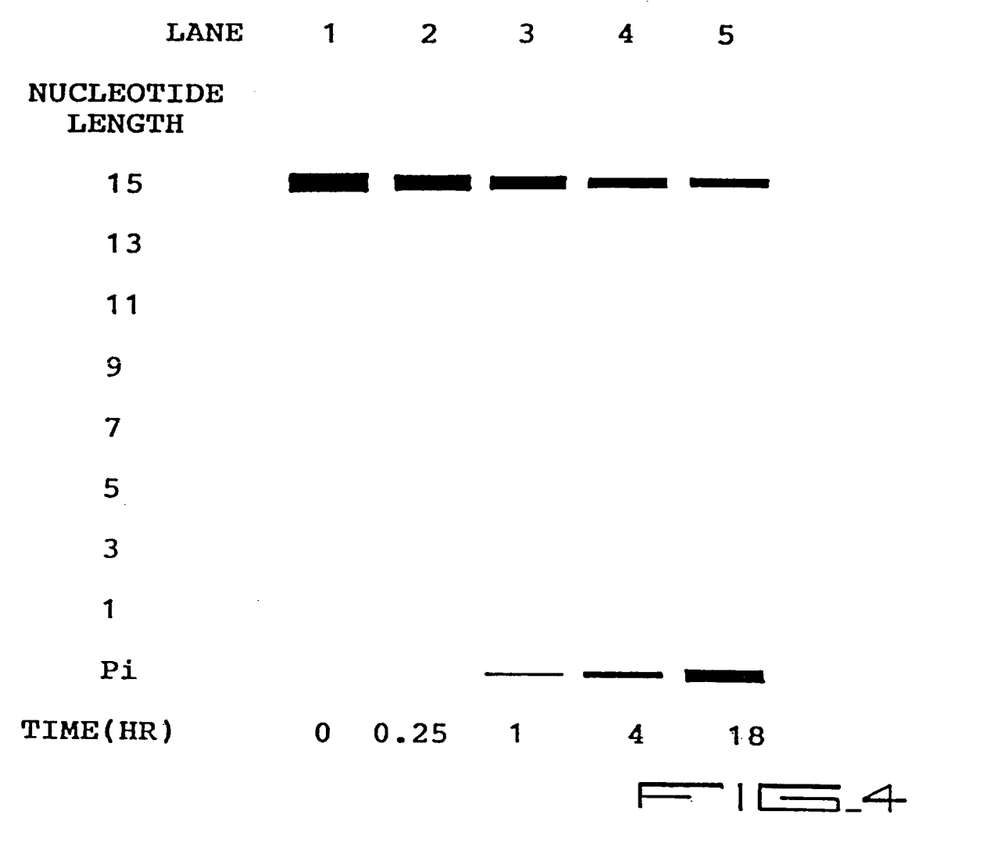
FIG. 4 is a drawing of an autoradiogram demonstrating that an oligonucleotide in which only the 3'-most internucleotide link is modified is completely resistant to degradation in human blood. The oligonucleotide is a derivative of MA-15 in which the 3'-terminal internucleotide link is a 2,2,2-trichloro-1,1-dimethylethyl phosphotriester. Lane 1 is the oligonucleotide prior to incubation. Lanes 2–5 are aliquots taken after incubation of the oligonucleotide in blood for 15 minutes, 1 hour, 4 hours, and 18 hours, respectively. The decrease in intensity of the original band is due simply to removal of the 5'-end label rather than degradation of the oligonucleotide. Pi is inorganic phosphate.

The modified oligonucleotide was labeled with $^{32}$P at the 5'-terminal OH group using $\gamma^{32}$P-ATP and T4 polynucleotide kinase as described in Example 3. The radiolabeled oligonucleotide was incubated in human blood at 37° C. Aliquots were removed at various times and analyzed by polyacrylamide gel electrophoresis. A drawing of the autoradiogram of the gel is shown in FIG. 4. No degradation of the oligonucleotide occurred over a period of 18 hours. The gradual decrease in the intensity of the band due to the full length molecule was due to removal of the $^{32}$P label from the oligonucleotide by a phosphatase present in blood, not to cleavage of the strand.

Similar studies were carried out in which the modified oligonucleotide was incubated in blood from the mouse. Again, no degradation of the oligonucleotide was observed.

EXAMPLE 6

Modification of Oligonucleotides at the 3'-Terminal Internucleotide Link Markedly Inhibits Their Degradation by Nucleases Present in Human Cells The derivative of MA-15 described in Example 5 in which the 3'-terminal internucleotide link was modified as a 2,2,2-trichloro-1,1-dimethylethyl phosphotriester was also used in this study. Extracts from K562 cells were prepared as in Example 4. The modified oligonucleotide was incubated in the cell extracts at 37° C. Aliquots were removed at various times, and the products of degradation were analyzed by polyacrylamide gel electrophoresis.

Degradation of this modified oligonucleotide by the rapid 3'- to 5'-exonuclease present in the cell extracts was completely blocked. This led to a marked increase in stability of the modified derivative compared to the native oligonucleotide. The half-life was prolonged by 10-fold. Degradation occurred by the slower 5'- to 3'-exonucleolytic activity present in the K562 cell extracts (see Example 4). The half-life for cleavage of the 5'-terminal nucleotide from the chain was about 20 minutes.

Similar studies were carried out in which the modified oligonucleotide was incubated in extracts prepared from COS cells (African green monkey kidney) and mouse liver cells. In both cases, the half-life of the derivative modified at the 3'-terminal internucleotide link was increased 10- to 15-fold compared to the unmodified oligonucleotide.

EXAMPLE 7

Oligonucleotides Modified at the 3'-Terminal Internucleotide Linkage Form Substrates with mRNAs That are Cleaved by RNaseH Mouse globin mRNA was isolated from mice rendered anemic by treatment with phenylhydrazine as described in Example 1. Three oligonucleotides were compared in this study; MA-15, the derivative of MA-15 utilized in Examples 5 and 6 in which the 3'-terminal internucleotide link is modified as a trichlorodimethylethyl phosphotriester (MA-15-TCDM), and a derivative further modified at the 5'-terminal OH group with naphthylisocyanate (NPH-MA-15-TCDM). Mouse globin mRNA (2 micrograms) was added to 1.1 nanomoles of the oligonucleotide in a final volume of 22 microliters containing 10 mM tris-HCl buffer at pH 7.5, 5 mM MgCl$_2$, 25 mM NaCl, and 1 mM dithiothreitol. The reactions were initiated by the addition of 2 units of *E. coli* RNaseH, and were allowed to proceed for 30 minutes at 37° C. The reactions were stopped by extraction of the samples with a 1:1 mixture of phenol and chloroform. The mRNA species remaining after digestion with RNaseH were isolated by precipitation with ethanol and analyzed on Northern blots.

Figure 5:
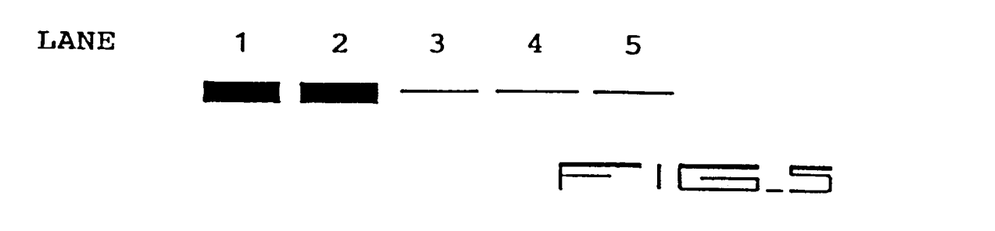
FIG. 5 is a drawing of an autoradiogram of a Northern blot demonstrating that oligonucleotides modified at the 3'-internucleotide link form substrates with mRNAs that are acted upon by RNaseH resulting in cleavage of the mRNA at the site of the RNA-DNA double helix. Lane 1 is mouse globin mRNA alone. Lane 2 is mouse globin mRNA incubated with RNaseH in the absence of oligonucleotide. Lane 3 is globin mRNA hybridized with MA-15 and cleaved with RNaseH. In lane 4, the substrate for RNaseH is formed with the derivative of MA-15 in which the 3'- terminal internucleotide link is a trichlorodimethylethyl phosphotriester. In lane 5, the oligonucleotide used was further modified with naphthylisocyanate at the 5'-OH group of the molecule. Samples were electrophoresed on a 1.5% agarose gel. After electrophoresis the gel was blotted onto GENE SCREEN PLUS™ (DuPont), and bands were localized using $^{32}P$ labeled MA-15 as a probe for α-globin mRNA.

The RNA samples were reacted with 1 M glyoxal in a 1:1 (volume/volume) mixture of 10 mM sodium phosphate buffer at pH 6.5 and dimethylsulfoxide for 1 hour at 50° C., and then electrophoresed on a 1.5% agarose gel. The RNAs were transferred from the gel to a Gene Screen Plus filter (DuPont-NEN) by capillary blotting according to the method described by the manufacturer. Prehybridization of the filter was done in 1% sodium dodecylsulfate, 1 M NaCl, 10% dextran sulfate, 50 mM sodium phosphate pH 6.5 for 2 hours at 35° C. Hybridization was conducted in 5 ml of the prehybridization buffer containing 200 microgram/ml denatured salmon sperm DNA plus 2×10$^6$ counts/min of MA-15, radiolabeled with $^{32}$P at the 5'-end of the molecule, for 24 hours at 35° C. After the hybridization, the filter was washed in the following order: once in 2×SSC (0.15 M NaCl, 0.015 M sodium citrate) for 5 minutes at room temperature, twice in 2×SSC plus 1% sodium dodecylsulfate for 30 minutes at 35° C., and once in 0.1×SSC for 5 minutes at room temperature. The filter was blotted dry and exposed to KODAK® XAR-5 film for autoradiography. A drawing of the autoradiogram is shown in FIG. 5.

Using radiolabeled MA-15 as a probe, a single band due to α-globin mRNA was detected on the Northern blot. In the absence of oligonucleotide, no cleavage of the mRNA occurred during the incubation with RNaseH (lane 2). For the reaction in the presence of MA-15 (lane 3), a marked decrease in the intensity of the band for α-globin mRNA is observed due to the cleavage of the mRNA by RNaseH at the site of hybridization with the probe. A similar decrease in intensity of the α-globin mRNA band was observed for the reactions with each of the modified oligonucleotides (lanes 4 and 5), indicating that they also hybridize with the mRNA to form a substrate that is recognized and cleaved by RNaseH.

EXAMPLE 8

Inhibition of Expression of the C-MYC Oncogene in the Murine Plasmacytoma Cell Line MOPC 315 with Complementary Oligonucleotides Modified at the 3'-Terminal Internucleotide Link

C-myc is a cellular oncogene aberrantly expressed by a number of human and animal tumor cells both in vivo and in cell culture. In the case of the murine plasmacytoma cell line MOPC 315, the c-myc gene is translocated from its normal position on chromosome 15 to the immunoglobulin locus on chromosome 12 and is expressed at an abnormally high level.

Two oligonucleotide analogs complementary to the sequence of c-myc mRNA coding for amino acid residues 191 to 198 were synthesized:

5'-(PN)-GTAGGGAAAGACCACTGAGGGT^C where (^) represents a trichlorodimethylethyl phosphotriester and (PN)=

The TCDM phosphotriester was incorporated into the chain by the procedure described in Example 5. The remaining portion of the sequence containing unmodified phosphodiester groups was synthesized by the phosphoramidite method. The 5'-terminal group (PN) was introduced using the reagent Aminolink from Applied Biosystems according to the procedure described by the manufacturer. For comparison, the unmodified oligonucleotide having the same base sequence was also prepared, as well as an oligonucleotide complementary to human albumin mRNA:

where (^) again represents the TCDM group.

MOPC 315 cells were maintained in RPMI 1640 culture media containing 10% fetal calf serum at 37° C. with 7% $CO_2$. Log phase MOPC 315 cells were harvested by centrifugation (250×g for 19 minutes at 23° C.) and resuspended at a density of 5×10$^6$/ml in HB101 serum-free medium (DuPont). One ml aliquots of this cell suspension were incubated in the presence of oligonucleotide for 4 hours at 37° C. and 7% $CO_2$. Additional one ml aliquots were incubated concomitantly without oligonucleotide. Cells from each group were then collected by centrifugation. Total cellular RNA was prepared as described by Chirgwin et al., Biochemistry 18, 5294–5299 (1979), and analyzed by Northern blots as described in Example 7. The filters were probed with an oligonucleotide complementary to c-myc mRNA labeled with $^{32}$P using polynucleotide kinase and γ$^{32}$P-ATP as in previous examples.

Both of the anti-c-myc oligonucleotides modified at the 3'-terminal internucleotide link with the TCDM group, at a concentration of 1 micromolar, decreased the level of c-myc mRNA by 75% when compared to the steady-state level of the mRNA in MOPC 315 cells incubated in the absence of oligonucleotide. The unmodified oligonucleotide against c-myc and the anti-albumin oligonucleotide had no effect on c-myc mRNA levels at a concentration of either 1 or 5 micromolar. This result is consistent with recent studies of another lymphoid cell line in which no inhibition of expression of the c-myc gene was found at concentrations of an unmodified anti-c-myc oligonucleotide below a concentration of 15 micromolar (Heikkila et al. (1987) Nature 328, 445–449). The modified derivatives described herein, thus, are between 20- and 50-fold more effective at inhibiting the expression of a targeted gene in intact cells than is the corresponding unmodified oligonucleotide.

In summary, the results presented show that oligonucleotides in which the 3'-terminal phosphodiester linkage is modified are resistant to nuclease digestion within cells and body fluids, retain normal hybridization properties with complementary nucleic acid sequences, and when hybridized to specifically targeted mRNA species form substrates which are recognized and cleaved by the enzyme RNaseH, enabling the oligonucleotide to be used to block the expression of the corresponding gene as is desired in various therapeutic applications.

Other modifications of the oligonucleotide may be made without departing from the scope and spirit of the invention, the important factor and contribution being the discovery that modification of the 3'-terminal phosphodiester linkage alone is sufficient to markedly increase the resistance of the oligonucleotide to degradation, and that such derivatives are able to form substrates with RNAs that are recognized and cleaved by RNaseH. Additional substituents may be added to further increase the stability of the oligonucleotide against degradation, to facilitate intracellular transport, or to attach labels, e.g., radioactive, fluorescent, or enzyme markers, for use of the oligonucleotide as a hybridization probe in diagnostic tests. It is important that such further modifications be restricted to a limited number of other sites on the molecule. If most or all of the phosphate groups within the chain are modified, the hybridization properties of the oligonucleotide may be adversely affected, and it will not form substrates with mRNAs that are acted upon by RNaseH. This latter fact defeats the use of highly modified oligonucleotide analogs as therapeutic agents to block the expression of specifically targeted genes.

It therefore can be seen that the invention accomplishes at least all of the objectives heretofore stated.

What is claimed is:

1. A method of decreasing expression of a targeted gene in a eukaryotic cell which expresses the targeted gene comprising:

contacting the cell with an oligodeoxynucleotide, which oligodeoxynucleotide has (a) complementarity for and is hybridizable to an mRNA region within mRNA transcribed from the targeted gene, such complementarity being sufficient to ensure specificity of hybridization of the oligodeoxynucleotide to the region within the mRNA transcribed from the targeted gene;

(b) a modified 3'-terminal internucleotide linkage, which linkage is resistant to 3' to 5' exonuclease degradation; and (c) a continuous stretch of at least five nucleotide residues having four internucleotide phosphodiester linkages which are unmodified; wherein said oligodeoxynucleotide, when hybridized with an RNA molecule for which it has complementarity under conditions in which an RNaseH is active, forms a substrate that can be cleaved by the RNaseH, under conditions such that said oligodeoxynucleotide decreases the expression of the targeted gene in the eukaryotic cell relative to the expression of the targeted gene in the eukaryotic cell not contacted with the oligodeoxynucleotide.

2. The method of claim 1 wherein the eukaryotic cell is in a living animal.

3. The method of claim 1 wherein the modified 3'-terminal internucleotide linkage of the oligodeoxynucleotide is a phosphotriester, phosphonate, phosphoramidate, phosphorothioate, or phophoroselenate linkage.

4. The method of claim 1 wherein the oligodeoxynucleotide further contains one or more additional modification(s), which additional modification(s) confers resistance to nuclease degradation.

5. The method of claim 4, wherein the additional modification(s) of the oligodeoxynucleotide is/are an additional modified internucleotide linkage.

6. The method of claim 5 wherein the additional modified internucleotide linkage of the oligodeoxynucleotide is at the 5'-terminal internucleotide linkage.

7. The method of claim 5 wherein the additional modified internucleotide linkage of the oligodeoxynucleotide is a phosphotriester, phosphonate, phosphoramidate, phosphorothioate, or phosphoroselenate linkage.

8. The method of claim 1 wherein the oligodeoxynucleotide further contains one or more additional modification(s), which additional modification(s) enhance(s) membrane crossing ability of said oligodeoxynucleotide, thus facilitating transport of said oligodeoxynucleotide into the cell.

9. The method of claim 8, wherein the additional modification(s) of the oligodeoxynucleotide is/are an additional modified internucleotide linkage.

10. The method of claim 8, wherein the additional modification of the oligodeoxynucleotide is a modification of the oligodeoxynucleotide 5' terminal —OH group.

11. The method of claim 9 wherein the additional modified internucleotide linkage is present within the oligodeoxynucleotide such that the continuous stretch of unmodified internucleotide linkages is flanked by nuclease resistant internucleotide linkages.

12. The method of claim 9 wherein the additional modified internucleotide linkage of the oligodeoxynucleotide is at the 5'-terminal internucleotide linkage.

13. The method of claim 1 wherein the oligodeoxynucleotide is from about 10 to about 75 nucleotides in length.

14. The method of claim 1 wherein the oligodeoxynucleotide is attached to a carrier molecule, which carrier molecule is taken up by a cell.

15. The method of claim 1 wherein the oligodeoxynucleotide continuous stretch is of greater than eight nucleotide residues having greater than seven internucleotide phosphodiester linkages which are unmodified.

16. The method of claim 1 wherein all oligodeoxynucleotide internucleotide linkages outside the continuous stretch are modified.

17. A method of decreasing expression of a targeted gene in a eukaryotic cell which expresses the targeted gene comprising:

contacting the cell with an oligonucleotide, which oligonucleotide has (a) complementarity for and is hybridizable to an mRNA region within mRNA transcribed from the targeted gene, such complementarity being sufficient to ensure specificity of hybridization of the oligonucleotide to the region within the mRNA transcribed from the targeted gene;

(b) a first continuous stretch of at least five nucleotide residues, wherein said first continuous stretch, when hybridized with an RNA molecule for which it has complementarity under conditions in which an RNaseH is active, forms a substrate that can be cleaved by the RNaseH; and (c) a second continuous stretch of nucleotide residues, 3' to the first continuous stretch, which second continuous stretch: (1) has a 3'-terminal internucleotide linkage which is resistant to 3' to 5' exonuclease degradation; and (2) when hybridized with an RNA molecule for which it has complementarity under conditions in which an RNaseH is active, does not form a substrate that can be cleaved by RNaseH, under conditions such that said oligonucleotide decreases the expression of the targeted gene in the eukaryotic cell relative to the expression of the targeted gene in the eukaryotic cell not contacted with the oligonucleotide.

18. The method of claim 17 wherein the first continuous stretch is greater than eight nucleotide residues.

19. The method of claim 17 wherein the second continuous stretch of the oligonucleotide contains one or more internucleotide linkages, in addition to the 3'-terminal internucleotide linkage, which is/are nuclease resistant.

20. The method of claim 17 wherein all the internucleotide linkages of the second continuous stretch are nuclease resistant.

21. The method of claim 17, 18, 19, or 20 wherein the oligonucleotide contains a third continuous stretch of nucleotide residues, 5' to the first continuous stretch, which third continuous stretch has a 5'-terminal internucleotide linkage which is resistant to 5' to 3' exonuclease degradation.

22. The method of claim 21 wherein the third continuous stretch of the oligonucleotide contains one or more internucleotide linkages, in addition to the 5'-terminal internucleotide linkage, which is/are nuclease resistant.

23. The method of claim 21 wherein all the internucleotide linkages of the third continuous stretch are nuclease resistant.

24. The method of claim 18 wherein the first continuous stretch is between about 17 and 21 nucleotide residues.

25. The method of claim 1 or 17, wherein the RNaseH is *Escherichia coli* RNaseH and the conditions in which it is active comprise a temperature of 37° C. and a buffered solution selected from the group consisting of:

a) a buffered solution of pH 7.5, comprising 5 mM $MgCl_2$, 25 mM NaCl and 1 mM dithiothreitol; and b) a buffered solution of pH 8.0, comprising 20 mM KCl, 9 mM $MgCl_2$ and 1 mM 2-mercaptoethanol.

\* \* \* \* \*